United States Patent [19]

Grayzel

[11] Patent Number: 4,850,960
[45] Date of Patent: Jul. 25, 1989

[54] DIAGONALLY TAPERED, BEVELLED TIP INTRODUCING CATHETER AND SHEATH AND METHOD FOR INSERTION

[76] Inventor: Joseph Grayzel, 262 Fountain Rd., Englewood, N.J. 07631

[21] Appl. No.: 71,040

[22] Filed: Jul. 8, 1987

[51] Int. Cl.$^4$ ............................................. A61M 25/00
[52] U.S. Cl. ..................................... 604/53; 128/343; 604/158; 604/280
[58] Field of Search .................................. 604/51–53, 604/158–170, 264, 280, 272–274; 128/343

[56] References Cited

U.S. PATENT DOCUMENTS

| | | | |
|---|---|---|---|
| 387,454 | 8/1888 | Siegenthaler | 604/164 X |
| 2,269,823 | 1/1942 | Kreiselman | 128/207.15 |
| 2,512,569 | 6/1950 | Saffir | 604/272 |
| 2,828,744 | 4/1958 | Hirsch et al. | 604/165 |
| 3,093,134 | 6/1963 | Roehr | 604/272 |
| 3,204,634 | 9/1965 | Koehn | 604/164 |
| 3,395,711 | 8/1968 | Plzak | 128/200.26 |
| 3,401,687 | 9/1968 | Hood | 128/79 |
| 3,921,631 | 11/1975 | Thompson | 604/53 |
| 4,146,034 | 3/1979 | Gupta | 128/207.14 |
| 4,243,050 | 1/1981 | Littleford | 604/164 X |
| 4,548,602 | 10/1985 | Ring | 604/280 |
| 4,581,025 | 4/1986 | Timmermans | 128/264 |
| 4,602,624 | 7/1986 | Naples et al. | 128/784 |
| 4,629,450 | 12/1986 | Suzuki et al. | 604/164 |
| 4,645,491 | 2/1987 | Evans | 604/273 |

*Primary Examiner*—Dalton L. Truluck
*Attorney, Agent, or Firm*—Weingram & Zall

[57] ABSTRACT

The present invention provides an improved introducing-dilating catheter which may also be applied to facilitate insertion of catheters of all types and functional purposes. The catheter has a tapered portion which is, in turn, connected to a bevelled tip portion to facilitate insertion of the catheter into a pre-existing puncture aperture. The bevelled tip portion is finished to remove any points capable of puncturing or any edges capable of injuring the tissues by the application of only a small force. Indicia means are provided to enable the practitioner using the introduction-dilation catheter to determine the orientation of the tip of the catheter so that the leading point of the bevelled tip will initiate engagement with the vascular puncture cut and enter the vessel in the acute angle formed between the guide wire and the vessel wall. Additionally, after entry of the entire tip, the indicia means allow the introducing catheter to be reoriented so as to keep the bevel parallel to the wall of a vessel.

26 Claims, 3 Drawing Sheets

DIAGONALLY TAPERED, BEVELLED TIP INTRODUCING CATHETER AND SHEATH AND METHOD FOR INSERTION

BACKGROUND OF THE INVENTION

1. Field of the Invention

The present invention relates to introducing catheters and specifically to such a catheter having a bevelled introducing tip, a cylindrical portion between the end of the bevel and a tapered portion. Visible indicia are provided on the introducing catheter, the indicia starting at the tip. The invention also relates to introducing sheaths having a bevelled introducing tip and visible indicia to locate the position of the bevel.

2. Description of the Prior Art

Insertion of catheters into blood vessels is frequently done by the percutaneous method, a procedure comprising a series of steps as follows:

(1) A needle punctures the skin and is directed into the blood vessel, such entry generally heralded by the back-flow of blood through said needle.

(2) A fine guide wire in the form of a tightly coiled helix is inserted within said needle, enters said blood vessel where it is advanced so that a portion lies securely within the blood vessel for some length while the remainder lies above the skin surface.

(3) The needle is withdrawn while the guide wire remains in place, partly within said blood vessel and extending proximally through the skin.

(4) A so-called introducnng or dilating catheter with tapered tip is threaded over the proximal end of the guide wire and advanced along the guide wire as its tip passes through the skin, subcutaneous tissue, and blood vessel wall to enter the lumen of the blood vessel continually guided by the flexible helical wire. The purpose of this introducing and/or dilating catheter is to expand the vascular puncture hole so that it will accommodate the operational diagnostic or therapeutic catheter to be finally inserted.

Introducing catheters presently in use are chosen with an outer diameter identical to that of the operational catheter, but the introducing catheter possesses a tip which tapers down to the outer diameter of the guide wire. The present art for such a tapered tip is exclusively that comprising a taper which is radially symmetrical. The taper involves both the lumen and the wall of the introducing-dilating catheter over a length of approximately 20 mm. Therefore, when passed over the guide wire into the blood vessel, a sufficient portion of he introducing-dilating catheter is inserted into the blood vessel so that the entire tapered tip as well as some portion of the full diameter of the catheter lies within said vessel, thereby insuring that the vascular puncture hole has been dilated to the full diameter of the catheter.

(5) A thin-walled outer tubular member, called a sheath, is passed over the proximal end of the introducing-dilating catheter, to whose diameter it fits precisely, and then the sheath and catheter are advanced through the skin, subcutaneous tissue and blood vessel wall until its distal portion of the sheath enters the lumen of said blood vessel.

(6) The introducing catheter and internal guide wire are quickly removed from the sheath while maintaining the position of the tubular sheath within the blood vessel, and the operational catheter is inserted via the sheath into the blood vessel, from whence it can be manipulated to other locations within the circulatory system.

Many patents have issued for apparatus relating to inserting and/or dilating catheters.

Thompson U.S. Pat. No. 3,921,631 shows a device for insertion of catheters using a hollow slotted needle. This is a so-called "through-the-needle" catheter insertion apparatus. The needle tip 20 is bevelled to form a cutting edge which results in a shearing or slicing action when forming the puncture hole rather than a tearing action, so as to produce a smooth puncture rather than a ragged puncture. A varying diameter tapered section is employed at the distal end of the catheter hub to seal the space between the needle and the catheter to prevent bleeding.

Suzuki et al. U.S. Pat. No. 4,629,450 discloses an instrument comprising an inner needle with a tip formed to include a cutting edge, and a dilator portion having a hollow dilator with a tip for enabling the inner needle to be passed therethrough until the cutting edge of the inner needle projects from the tip of the dilator. As discussed in the patent, the cutting tip of the inner needle makes the initial puncture of the vessel. The inner needle is then withdrawn leaving the dilator portion in place. A guide wire is then inserted through the dilator. A secondary thicker portion of the dilator is then inserted along the guide wire to widen the opening. The dilator is then withdrawn and the catheter is inserted over and along the guide wire.

Both of these patents deal with bevels of the initial puncturing member which are metallic needles. The present art for fabricating the tapered tip of an introducing-dilating catheter as used in (4) of the percutaneous method described above is exclusively that comprising a taper which is radially symmetrical, and ending in a tip cut off at a right angle to the longitudinal axis of the catheter. Although the wall of the catheter, as well as the lumen within, is tapered to present the smallest profile when engaging the puncture hole, the limited strength of the flexible plastic material of which these catheters are made necessarily limits the degree to which the wall can be thinned down. Hence, the catheter tip presents as a blunt step upon attempting to enter the puncture hole over the guide wire. Although, approaching the artery at an acute angle of approximately 35°, the elasticity of the blood vessel permits some movement of the vessel wall at the acute angle such that the entire blunt circumference of the catheter tip is pressing against the entire circumference of the puncture hole as force is applied to effect entry of the catheter. Often, the required force is considerable and the catheter generally pops through the puncture hole suddenly with a palpable abruptness. This may cause additional trauma or tearing at the puncture site.

This introducing problem is again encountered when positioning the sheath over the catheter within the lumen of the blood vessel.

SUMMARY AND OBJECTS OF THE INVENTION

The present invention, to overcome the problems set forth, provides an improved introducing-dilating catheter which may also be applied to facilitate insertion of catheters of all types and functional purposes. The catheter has a tapered portion which is, in turn, connected to a bevelled tip portion to facilitate insertion of the catheter into a pre-existing puncture aperture. The bevelled tip portion is finished to remove any points capable of puncturing or any edges capable of injuring the tissues by the application of only a small force. Indicia means are provided to enable the practitioner using the introduction-dilation catheter to determine the orientation of the tip of the catheter so that the leading point of the bevelled tip will initiate engagement with the vascular puncture cut and enter the vessel in the acute angle formed between the guide wire and the vessel wall. Additionally, after entry of the entire tip, the indicia means allow the introducing catheter to be re-oriented once inserted into the vessel so as to keep the bevel parallel to the wall of a vessel.

The present invention also sets forth a sheath with a bevelled introducing tip and visible indicia to indicate the position of the tip, which sheath functions during introduction in much the same manner as the bevelled tip introducing catheter, to achieve the same beneficial results relating to ease of entry and proper positioning.

Accordingly, it is an object of the present invention to provide an introducing catheter and/or sheath having a bevelled tip surface which is formed in either a planar or a concave configuration.

Yet another object of the present invention is to provide an introducing catheter and/or sheath having a bevelled tip surface in which the end of the bevel rearmost from the tip is chamfered to provide a smoother surface for introduction into the body.

Still another object of the present invention is to provide an introducing catheter which has a cylindrical portion between the tapered portion and the bevelled tip thereof.

A further object of the present invention is to provide an introducing catheter which separates the entry function of the catheter from the dilation function of the catheter.

Yet a further object of the present invention is to provide an introducing catheter which spaces the entry tip of the catheter from the tapered dilating portion of the catheter.

Another object of the present invention is to provide an introducing catheter which is utilized after the catheter guide wire is inserted into the vessel, the initial surfaces contacting the skin being such that minimal force is required to insert the introducing catheter into the vessel.

Still another object of the present invention is to provide a catheter and/or sheath having a bevelled tip surface which is formed in the shape of either a plane or in a concave manner, the end of the bevel rearmost from the tip being optionally chamfered to provide still smoother surfaces for introduction into the body.

A still further object of the present invention is to provide a bevelled introducing catheter which cooperates with the guide spring residing in the vessel.

A still further object of the present invention is to provide a bevelled introducing catheter and/or sheath with an indicator visible along the introducing catheter to provide proper orientation of the bevel relative to the vessel.

Another object of the present invention is to provide an insertion catheter and/or sheath which has an indicator constituted by a colored stripe running the entire length of the introducing catheter.

A further object of the present invention is to provide an introducing catheter and/or sheath which, if desired, may have a hardened tip portion to facilitate introduction in some applications.

It is yet another object of the present invention to provide a bevelled introducing catheter and/or sheath which eases introduction of the catheter and/or sheath, especially with regard to passage through the muscle wall of the vessel through which the catheter is placed.

Still another object of the present invention is to provide an introducing catheter and/or sheath which reduces the risk of tearing the vessel wall at initial introduction of the tip of the catheter and/or sheath, which introduction by the catheter is done to enlarge the size of the puncture in the wall of the vessel.

A further object of the present invention is to provide an introducing catheter and/or sheath which is safer because it reduces the chance of injury to the rear wall of the vessel in which it is inserted, such as with abrasion resulting from contact with the leading edge or tip of the catheter and/or sheath during movement with the vessel, as for example which occurs with the catheter during passage of the tapered dilating portion of the device.

Still another object of the present invention is to provide an inserting catheter and/or sheath which minimizes the size of the hole by causing the catheter to be introduced atraumatically, permitting enlargement of the puncture hole by elastic dilatation rather than by tearing.

Yet another object of the present invention is to provide an insertion catheter and/or sheath which provides better control during introduction by reducing the axial force necessary to penetrate the muscular wall of the vessel into which it is introduced.

It is yet another object of the present invention to provide a bevelled insertion catheter and/or sheath which is safer to use because it provides indication of the orientation of the bevelled leading point.

A further object of the present invention is to provide a bevelled insertion catheter and/or sheath which is safer because it allows rotation of the bevelled leading point to the optimum position for safety after full insertion of the catheter.

Still another object of the present invention is to provide an insertion catheter and/or sheath having indicia to indicate rotational orientation of the tip of the catheter disposed at a plurality of radial locations along the circumference of the catheter.

Yet another object of the present invention is to provide an insertion catheter and/or sheath having primary, secondary and tertiary indicia for the location of the bevel at the insertion tip of the catheter and/or sheath.

A further object of the present invention is to provide an insertion catheter having a bevelled tip wherein the bevelled tip has a strengthened and/or hardened insertion portion.

Another object of the present invention is to provide an insertion catheter having a bevelled tip wherein the bevelled tip has a strengthened and/or hardened insertion portion where the tip is formed from a composite of plastic and another material such as metal or a ceramic.

Still another object of the present invention is to provide an insertion catheter having a bevelled tip wherein the tip of the bevelled catheter is strengthened and/or hardened by metallic plating.

Yet another object of the present invention is to provide an insertion catheter having a bevelled tip wherein the tip of the catheter is strengthened and/or hardened by irradiating the tip to increase the cross-linking of the polymer used to form the catheter.

Another object of the present invention is to provide a bevelled introducing catheter and/or sheath wherein the bevel can be positioned during various stages of the insertion procedure.

A further object of the present invention is to provide an insertion dilation catheter having a tapered dilating portion in which the taper is entirely on the outer surface of the dilating portion of the catheter.

Still another object of the present invention is to provide an insertion dilation catheter having a tapered outer portion with a fine bore of substantially constant diameter extending at least partially through the tapered outer section; and also having a conical bore segment which communicates the fine inner bore to the larger bore of the catheter. The conical bore segment facilitates the threading of guide wires into the constant diameter bore.

Yet another object of the present invention is to provide a method of inserting a bevelled catheter and/or sheath into a blood vessel by a percutaneous procedure in which the catheter can be inserted with the point of the bevel positioned for optimum entry and then rotated to minimize the likelihood of contact injury by the pointed end of the bevel with the back wall of the vessel into which the bevelled end has been inserted.

Another object of the present invention is to provide a method of sequentially inserting an introducing catheter and a sheath into a blood vessel by a percutaneous procedure in which the catheter can be inserted with the point of the bevel positioned for optimum entry and then rotated to minimize the likelihood of contact injury by the pointed end of the bevel to the back wall of the vessel. After insertion of the catheter, the sheath can be inserted by sliding it over the catheter if the sheath is not already on the body of the catheter. Then the catheter and sheath advance as a unit with the point of the sheath bevel positioned for optimum entry and then rotated to minimize the likelihood of contact injury by the pointed end of the bevel to the back wall of the vessel into which the bevel end has been inserted. After insertion of the sheath, the introducing catheter and guide wire are removed, leaving the sheath in place.

These as well as additional object and advantages will be understood from a review of the accompanying detailed specification, reference being made to the accompanying drawings.

DETAILED DESCRIPTION OF THE INVENTION

Figure 1:
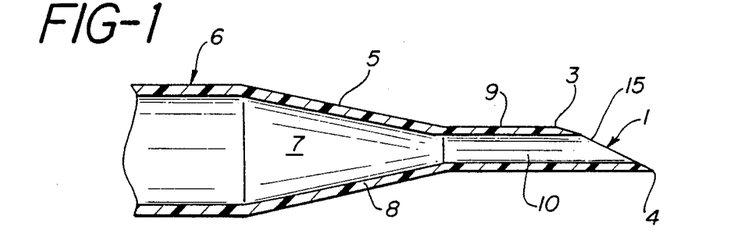
FIG. 1 is a side view in section of the introducing catheter of the present invention.
Figure 2:
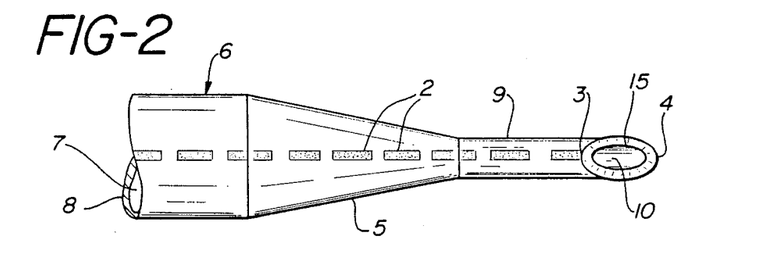
FIG. 2 is a top view of the introducing catheter of the invention.
Figure 3:
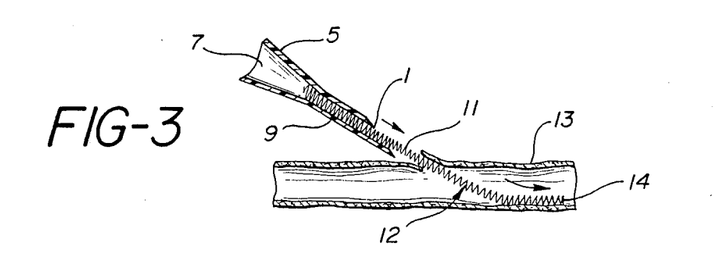
FIG. 3 is a view showing in section the catheter in use with a spring-guide in a blood vessel.

As shown in FIGS. 1 and 2, the improved introducingdilating catheter of the invention overcomes the disadvantages described above by possessing a bevelled tip 1, and a longitudinal stripe 2 in line with the rearmost point 3 of the bevelled end, hence 180° away from the leading point of the bevel, i.e. along the opposite side from the leading point 4 of the bevel. A distal 20 mm portion 5 of the catheter 6 is tapered with respect to both its inner lumen 7 with a constant wall thickness 8, similar to such tapers presently existing on introducing-dilating catheters. However, one difference in the taper of the present device is that the taper 5 is complete at a point several millimeters behind the tip, having attained an internal diameter 10 which matches the outer diameter 11 of the spring-guide 12 (FIG. 3). The last several millimeters at the tip is a truly cylindrical section 9, and it is in this portion that the diagonal bevel cut is made. With respect to the longitudinal axis of the catheter, the bevel 15 should be cut at an angle as acute as possible, preferably 30° or less.

The structure disclosed above is advantageous when inserted during a percutaneous insertion procedure (described above) by the following method. As shown in FIG. 3, following the third step of percutaneous insertion, the guide wire 12 alone remains in position through the skin, subcutaneous tissue, and blood vessel wall 13, with some length 14 lying within the lumen of said blood vessel. The patient is lying supine, thus placing blood vessels in the upper and lower extremities in the horizontal plane. The original needle puncture is made at an acute angle to the horizontal, generally in the range of 30° to 45°, and thus the guide wire 12 is disposed at this same angle.

In the fourth step of the procedure already described, an introducing-dilating catheter is passed over the guide wire to engage the vessel wall. Employing the invention, the introducingdilating catheter 6 is passed over the guide wire 12 with the longitudinal stripe 2 uppermost, clearly visible to the eye, and hence the leading point 4 of the bevel at the catheter's tip 1 is undermost, where it will engage the puncture hole in the vessel wall at the vertex of the acute angle between said vessel wall 13 and the guide wire 12. In this relationship, a minimum area of the catheter tip 1 engages the puncture hole at an acute angle along the underside of the guide wire 12. Therefore, it provides for a minimum force of entry. Thereafter, the remainder of the bevel tip 1 follows by gradual elastic enlargement of the puncture hole until the entire circumference of the tapered tip 1 is within the vascular lumen. Not only is the entry force minimized by the bevel tip 1, but the entry progresses gradually and easily, rather than suddenly with an impulsive discontinuous entry of the tip as now occurs with present art and methodology.

The principle of the bevelled tip may also be applied to construction of the so-called sheath, the thin-walled outer tubular member surrounding the introducing-dilating catheter, which slides over said catheter through the puncture hole, as described in step five above, to provide a final access channel to the blood vessel for insertion of the operational diagnostic or therapeutic catheter.

The novel aspect of the present art is not obvious in view of prior bevel art in medical instrumentation, particularly the bevelled cutting tip of needles such as shown in the aforementioned U.S. Pat. Nos. 3,921,631 and 4,629,450 or as used in hypodermic needles. Such bevelled tips are designed with a sharp, cutting edge around the circumference of the bevel and the leading point is sharp. Such bevels are intended for cutting and the sharp bevel cuts easily, for advancing the bevel causes a knife-like shearing force. The present bevel at the tip 1 of the introducing-dilating catheter 6 is not intended to cut and, in particular, the circumferential edge 15 of the bevel is rounded not sharp. Neither is the tip 1 pointed or sharp. The bevel disclosed herein is designed to effect a gradual spreading force on an existing puncture hole. The application of a bevel configuration employed for non-traumatic insertion into the vascular system is new art for such procedures. Its novelty is further attested by the fact that percutaneous insertion of catheters over guide wires has been practised for nearly 30 years since the technique was first described by Seldinger, yet the use of a bevelled introducing catheter tip to facilitate entry into the blood vessel has not been described or employed.

Entry of the bevelled tip 1 into a blood vessel is easier the more acute the angle of the bevel. However, with the limited strength of many thermoplastic materials employed in the fabrication of catheters, it may be desirable to strengthen the tapered tip of the catheter, particularly in the vicinity of and at the circumference of the bevel. While this is seen to be advantageous in the subject catheter disclosed herein, it may also be of use to strengthen the tip of other catheters where great flexibility or flaccidity of the tip is not essential. Strengthening the most distal portion of a catheter tip, such as the introducing-dilating catheter, may be accomplished by several means, such as by irradiation, for example gamma-radiation, selectively applied to the tip, such radiation causing increased cross-linking between and within molecules. Other techniques for cross-linking may also be used.

A firm tip may also be provided by a metallic plating of the plastic, as by electroplating.

A firm tip may also be provided by applying a coating of an agent which hardens upon curing, i.e. physico-chemical process.

A firm tip may also be attained by fabricating the rim of the bevel together with a small portion of the tip, of metal, ceramic, epoxy or other hard material and thn insert-molding of this tip into the thermoplastic body of the catheter.

Four types of configurations of the bevel are shown in FIGS, 4A-4D.

Figure 4A:
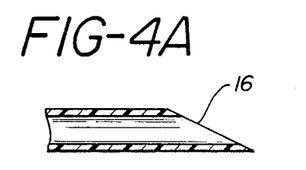
FIGS. 4A-4D are side views in section showing different configurations of bevels employed in the catheter.

In FIG. 4A, a planar bevel 16 is shown where the circumferential boundary of the bevel lies in a plane and the bevel, seen in profile, is a straight line.

Figure 4B:
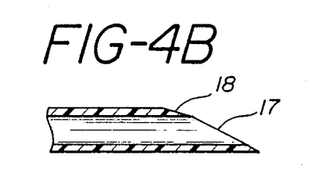

FIG. 4B shows a planar bevel 17 with a chamfer 18. This bevel 17 is similar to the simple planar bevel 16, with the additional feature comprising a rounding of the rearmost portion 18, thereby removing the corner angle created by a planar cut through the wall of the catheter's tip at the rearmost region of the bevel.

Figure 4C:
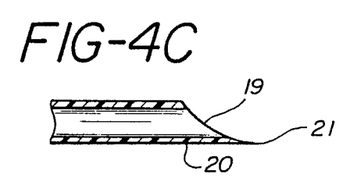

FIG. 4C employs a concave bevel 19. The bevel 19 is slightly cup-shaped with the edges of the cup, hence the concavity 20 facing forward, thereby accentuating the bevel's acute angle at its leading edge 21, further minimizing the forces of initial entry and proression of the bevel through the puncture hole.

Figure 4D:
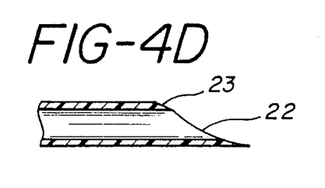

FIG. 4D uses a concave bevel 22 with a chamfer 23. This bevel 22 combines the concave profile described in FIG. 4C, with the chamfer described in FIG. 4B.

The modification of the bevel by the chamfer 18 or 23 at the rearmost region reduces the local profile of the bevel where it must pass beneath the upper lip of the arterial puncture hole and tereby eliminates the trauma associated with the transition from the bevel to the cylindrical portion 9 of the catheter.

Figure 5:
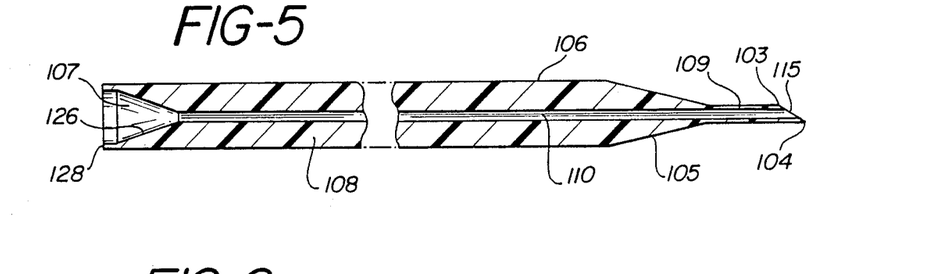
FIG. 5 is another embodiment of the invention similar to that shown in FIG. 1.

FIG. 5 shows another embodiment of the invention with modified construction. In this case, the catheter generally indicated at 106 has a thick-walled section 108 immediately behind the cylindrical portion 109 on which the bevelled tip 101 is formed. The external taper 105 occurs in the thick-walled section or at least a part of the thick-walled section of the catheter. The thick-walled section begins at the juncture of the externally tapered section 105 with the cylindrical section 109 and ends at the conical transition 126 of the lumen from the wide portion of the lumen 107 to the narrow portion of the lumen 110 that extends to the tip 101 of the catheter.

The walls 128 of the catheter about the larger lumen section 107 are relatively thin and may be in the same nature as the wall thickness of the catheter shown in FIG. 1. Most or all the external tapering from the main body of the catheter to the cylindrical tip section 109 occurs in the thick-walled section 108 of the catheter. The relative position of the internal conical section 126 with respect to the tapered external portion 105 determines the extent of the thickened wall portion 108 of the catheter.

The internally tapered section 126 facilitates the threading of a guide wire into the narrow lumen portion 110. The guide wire may merely be inserted in the rear of the catheter toward the front of the conical section 126 of the lumen which will guide the wire to the narrow portion 110 of the lumen that extends to the tip. The advantages of this thick-walled construction are that the catheter can be relatively sturdy and provide a relatively confined channel for the guide wire. The catheter will be able to take a greater axial force from the person controlling the catheter during the introductory procedure. Additionally, if the thick-walled portion extends almost the length of the catheter, then threading of the guide wire into the narrow portion 110 of the lumen is further facilitated.

As indicated in FIG. 5, other elements of the device include the walls of the bevel 115 with the forwardmost edge of the bevel 104 and rearmost edge 103. The outer constant diameter of the catheter is indicated as 106 with the wall between the enlarged lumen 107 and the outer diameter being indicated as 128.

Figure 6:
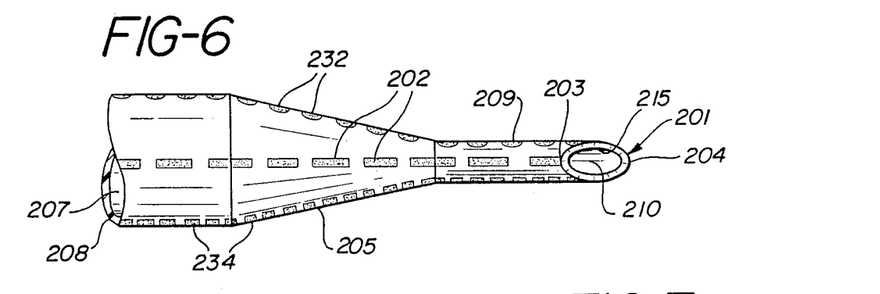
FIG. 6 is another embodiment of the invention similar to that shown in FIG. 2.

FIG. 6 shows another embodiment of the invention, similar to that shown in FIG. 2, but in which there are indicating means 202 in the form of a longitudinal stripe as in FIG. 2 but, in addition, indicating means disposed at approximately 90° angles at either side of the central indicating means. These are shown as a series of circles 232 and a series of squares 234. By having the three sets of indicating means disposed at 90° from each other, the physician-surgeon using the introducing catheter will always be aware of the position of the plane of the bevel 204 and therefore where the tip of the bevel 204 is with relation to the vascular puncture hole. Of course, two indicia disposed 180° apart could also be used rather than four indicia disposed at 90°.

The indicating means as shown in FIGS. 2 and 6 enable the introducing catheter to be manipulated to great advantage by the operator surgeon as shown in FIGS. 3, 7, 8 and 9. In FIG. 3, the bevelled edge of the introducing catheter is near the needle puncture and is moving for insertion along spring-guide 12. The leading edge 4 of the bevel is closest to the puncture hole to facilitate entry via the acute angle between the spring guide and vessel wall 13 as previously described.

Figures 7, 8, 9:
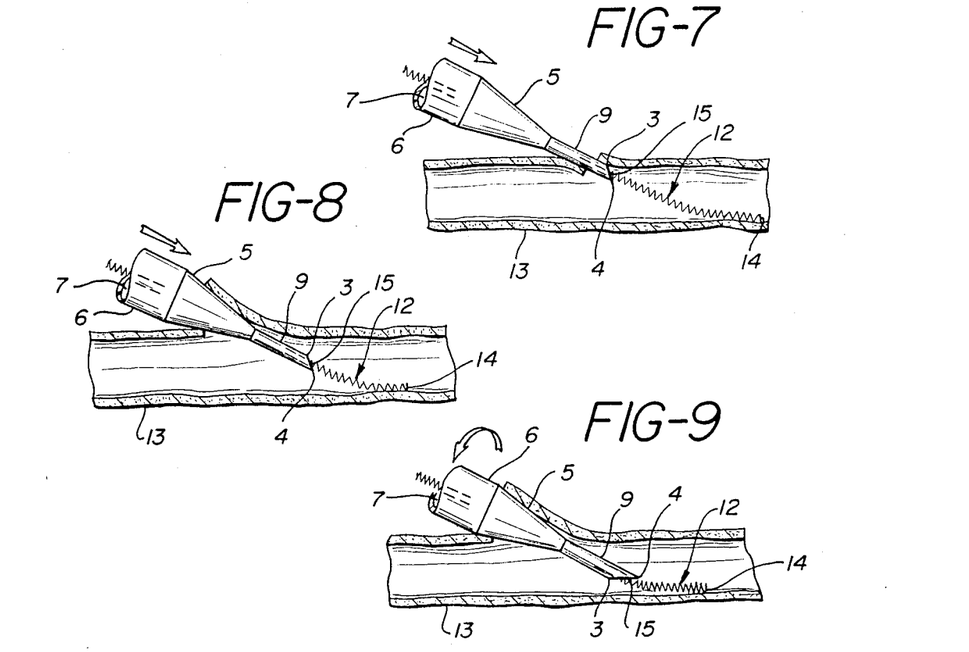
FIG. 7 is a view similar to FIG. 3 showing the initial entry stage of the catheter into the blood vessel.
FIG. 8 is a view similar to FIG. 7 showing an intermediate entry stage of the catheter int the blood vessel.
FIG. 9 is a view similar to FIG. 7 showing the catheter repositioned to minimize the angle between the bevel and the wall of the vessel to rotate the tip away from the wall.

As shown in FIG. 7, the catheter moves along the wire until the leading edge 4 has passed through the puncture of the blood vessel. In the initial entry position, the leading edge 4 of the catheter is in the lowermost position and below the spring-guide 14, and is the first point of the catheter to approach the puncture hole in the vessel.

As shown in FIG. 8, the catheter moves further along the wire as indicated by the arrow until the bevel from leading edge 4 to rear portion 3 is within the blood vessel. In this position, note that the narrow leading edge 4 is near the rear wall of the vessel and could easily come in contact with and/or damage the rear wall. Accordingly, as shown by the arrow on FIG. 9, the entire catheter is rotated 180°. Once the rotation occurs, as shown in FIG. 9, the plane of the bevel from leading edge 4 to end 3 will be repositioned to be parallel to the wall of the blood vessel. The leading edge 4 is rotated away from the wall of the vessel. Therefore it will be almost impossible for the leading edge 4 of tip 1 of the catheter to contact the wall of the vessel because the portion 14 of the springguide 12 that is within the vessel will be between the plane of the bevel and the wall of the vessel.

Figure 10:
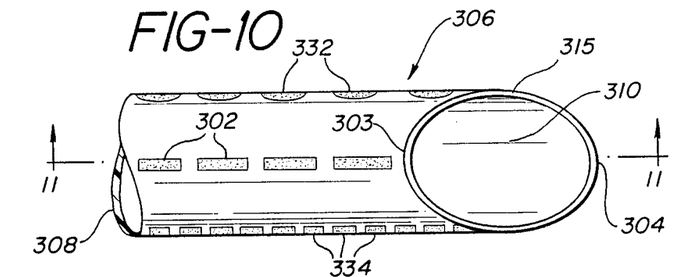
FIG. 10 is a top view of a sheath with a bevelled tip and indicia.
Figure 11:
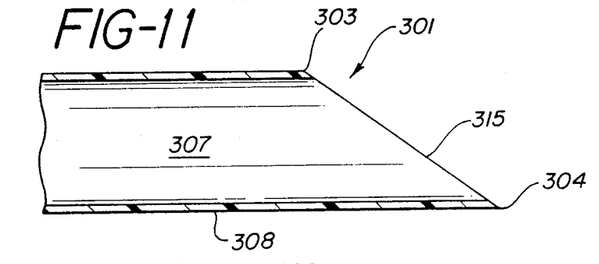
FIG. 11 is a side view in section of the sheath shown in FIG. 10.

FIGS. 10 and 11 show a sheath generally indicated at 306 having a bevelled tip 301 with an entry leading edge 304 and the rearmost portion of the bevelled tip 303. The wall of include the walls of the tapered bevel 115 with the forwardmost the sheath 308 is of a suitable material and it is of constant diameter enclosing a constant diameter lumen 307. Similar to the introducing catheter, the sheath is provided with visible indicia 302, 332 and 334 positioned at 90° intervals about the circumference of the catheter to indicate where the leading edge of the bevel 304 is positioned.

Figures 12, 13:
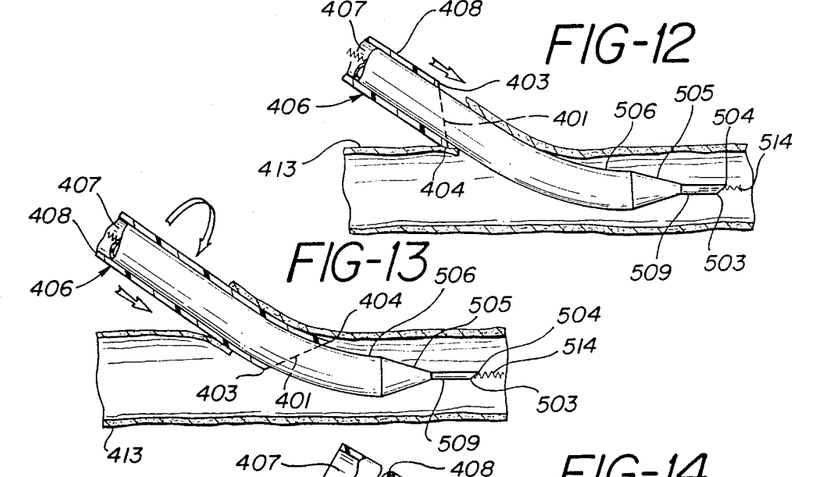
FIG. 12 is a view similar to FIG. 7 showing the sheath positioned on an introducing dilating catheter which has been placed in the lumen of the vessel, with the sheath about to make its initial entry into the blood vessel.
FIG. 13 is a view similar to FIG. 8 showing an intermediate entry stage of the sheath into the blood vessel.
Figure 14:
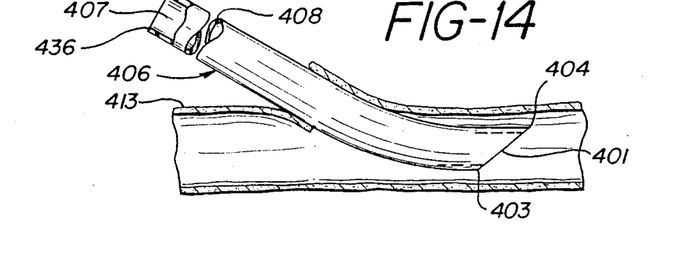
FIG. 14 is a view showing the sheath finally positioned within the lumen of the blood vessel and the introducing dilating catheter and guide wire withdrawn.

As shown in FIGS. 12, 13, and 14 the sheath is positioned in coaction with the introducing dilating catheter The introducing dilating cather generally indicated at 506 has been positioned sufficiently far within the lumen of the vessel so that the distal end of the catheter is generally parallel to the walls of the vessel. A sheath 406 is mounted on the tubular portion of the introducing dilating catheter 506 so that the wall of the sheath 408 is in contact with the tubular wall of the catheter 506. The sheath 406 is positioned well back from the insertion or distal end of the catheter.

After the distal end of the catheter has been fully inserted into the vessel, the sheath 406 and catheter 506 are moved together until the forwardmost portion of the bevelled tip 404 of the sheath and the rearmost portion 403 of the sheath have entered into the lumen of the blood vessel The sheath is then rotated in the same manner as was the introducing catheter so that the bevelled leading edge 404 of the sheath 406 is rotated away from close contact with the rear wall of the blood vessel to reduce the chance of injury to the vessel While sheath 406 is rotated, the leading edge 504 of the catheter 506 is fixed in place by holding the portion of the catheter extending beyond the proximal end 436 of sheath 406.

Once the sheath is in place, with the entry to the lumen of the blood vessel properly dilated and the opening is secured, the introducing dilating catheter 506 and the guide wire 514 can be removed leaving the sheath in place to allow for entry of the various devices that will then be placed into the blood vessel.

It is understood that the foregoing detailed specification is not intended to limit the spirit and scope of my invention. What is desired to be covered by United States Letters Patent is set forth in the appended claims.

What is claimed is:

1. An introducing catheter of a size for use in the vascular system for assisting in the insertion of other devices through the wall of blood vessels, said introducing catheter comprising:
   a flexible tubular body portion having a bore therethrough and a distal end and a proximal end, said bore constructed to coact with a guide element extending within the bore;
   a tapered portion extending from said distal end of said tubular body portion, said tapered portion having a diameter which gradually reduces along the length of the tapered portion forming a conical exterior shape;
   a tubular portion extending from the reduced diameter end of said tapered portion;
   a bevelled tip portion at the end of said tubular portion, said bevelled tip being formed at an acute angle with respect to the longitudinal axis of said tubular portion to facilitate entry into an existing puncture passage in the wall of a blood vessel; and
   said tapered portion operating to dilate the existing puncture passage in the wall of a blood vessel.

2. An introducing catheter of a size for use in the vascular system for assisting in the insertion of other devices through the wall of blood vessels, said introducing catheter comprising:
   a flexible tubular body portion having a bore therethrough and a distal end and a proximal end, said bore constructed to coact with a flexible guide element extending within the bore;
   a flexible guide implement extending within the bore of the tubular body portion;
   a tapered portion extending from said distal end of said body portion, said tapered portion having an outer diameter which gradually reduces along the length of the tapered portion, said tapered portion constructed and arranged to substantially dilate the exisitng puncture passage in the wall of a blood vessel; and
   a bevelled tip portion communicating with the narrow end of said tapered portion said bevelled tip being formed at an acute angle with respect to the longitudinal axis of said tubular portion to facilitate entry into an existing puncture passage in the wall of a blood vessel.

3. An introducing catheter of a size for use in the vascualr system for assisting in the insertion of other devices in blood vessels through the wall of the blood vessel, said introducing catheter comprising:

a flexible tubular body having a bore theretrough and a distal end and a proximal end, said bore constructed to coact with a guide element extending within the bore;

a tapered portion extending from said distal end of said body portion, said tapered portion having an outer diameter which gradually reduces along the length of the tapered portion;

a tubular portion extending from the reduced diameter end of said tapered portion;

a bevelled tip portion at the end of said tubular portion said bevelled tip being formed at an acute angle with respect to the longitudinal axis of said tubular portion to facilitate entry into an existing puncture passage in the wall of a blood vessel;

the inner diameter of said tapered portion remaining relatively constant for at least a segment of said tapered portion; and said tapered portion operating to dilate the existing puncture passage in the wall of a blood vessel.

4. The introducing catheter of claims 1, 2 or 3 wherein said bevelled portion is a planar surface along the entire length of the bevel.

5. The device of claims 1, 2, or 3 wherein said bevelled portion is concave curving away from said distal end of said body.

6. The device of claims 1, 2, or 3 Wherein the rearmost surface of the bevel is chamfered.

7. The device of claims 1,2 or 3 wherein visible indicia are provided along the length of the introducing catheter.

8. The device of claim 7 wherein said indicia means comprise markings extending along the length of said introducing catheter.

9. The device of claim 7 wherein said indicia are axially disposed on said catheter and are radially positioned at one or more intervals.

10. The device of claim 7 wherein said visible indicia comprise at least one line of markings extending along the length of said introducing catheter, at least one of said lines being disposed 80° from the leading point of the bevelled tip of the catheter.

11. The apparatus according to claim 1, 2, or 3 wherein said bevelled tip portion is finished to remove any points capable of puncturing or to remove any sharp edges capable of cutting tissue by only the insertion of the bevel.

12. The introducing catheter of claim 3 wherein said relatively constant diameter segment of said inner diameter of said tapered section expands in a conical shape to enable threading of a guide wire into the inner diameter portion at the end of said tapered portion.

13. A sheath of a size for use in the vascular system for assisting in the insertion of other devices in blood vessels through the wall of the blood vessel, said sheath comprising:

a flexible catheter for use in the vascualr system;

said sheath having a flexible uniformly thin walled cylindrical shell body portion having a bore therethrough and a distal end and a proximal end, said bore constructed to coact with and be supported by said flexible catheter extending within the bore;

a bevelled tip portion formed on the distal end of said sheath, said bevelled tip being formed at an acute angle with respect to the longitudinal axis of said tubular portion, to facilitate entry into an existing puncture in the wall of a blood vessel.

14. The device of claim 13 wherein visible indicia are provided along the length of the sheath to indicate the position of the tip of the bevelled end.

15. The device of claim 14 wherein said visible indicia comprise at least one line of markings extending along the length of said introducing catheter, one of said lines being disposed 180° from the leading point of the bevelled tip of the catheter.

16. The device of claim 1, 2, 3, or 13 further comprising indicia on said body portion to indicate the orientation of said bevel.

17. An introducing catheter of a size for use in the vascular system for assisting in the insertion of other devices through the wall of blood vessels, said vessels, said introducing catheter comprising a flexible tubular body portion having a bore therethrough and a distal end and a proximal end, said bore constructured to coact with a the bore;

a tappered portion extending from said distal end of said tubular body portion, said tapered portion having a diameter which gradually reduces along the length of the tapered portion forming a concial exterior shape;

a tubular portion extending from the reduced diameter end of said tapered portion; and a bevelled tip portion at the end of said tubular portion, said bevelled tip being formed at an acute angle with respect to the longitudinal axis of said tubular portion to facilitate coaction with a guide element which extends through a puncture passage in the wll of the blood vessel;

said tapered portion operating to dilate the existing punctude passage in the wall of a blood vessel.

18. A method for inserting a tapered, bevelled catheter of a size for use in the vascular system into a vessel comprising:

puncturing the vessel with a needle;

feeding a guide wire through the neddle into the vessel;

withdrawing the needle from the vessel with the guide wire remaining in place;

introducing the tapered bevelled catheter into the vessel along said guide wire by inserting the loading edge of the bevelled tip of the catheter in the undermost position relative to the puncture hole to engage the vessel at the acute angle between the guide wire and the vessel wall;

inserting the entire bevelled portion of the catheter into the vessel; and inserting said tapered portion of said catheter into the puncture passage, said tapered portion operating to dilate the existing puncture passage in the wall of the blood vessel.

19. The method according to claim 18 wherein, after the step of introducing the tapered catheter into the blood vessel, the catheter is rotated in accordance with indicia to position the plane of the bevel at a substantially parallel relationship to the rear wall of the vessel.

20. The method ccording to claim 18 wherein:

in the step of introducing the tapered catheter into the vessel along said guide wire, the leading edge of the bevelled tip of the catheter is between the guide wire and the outer wall of the vessel prior to introduction into the vessel; and after the step of introducing the tapered catheter into the vessel along said guide wire, the leading edge of the bevelled tip of the catheter has been rotated so that the leading edge is above the guide wire and the wall of the vessel against which the guide wire is resting.

21. The method according to claim 18 wherein the guide wire lies between the pointed end of the bevel and the rear wall of the vessel, against which the guide wire rests.

22. The method according to claim 18 wherein after the step of inserting the entire bevelled portion and tapered portion and at least some part of the main tubular body of the catheter into the vessel, comprising the following additional steps:
 introducing a sheath having a bevelled end positioned over the introducing catheter to insert the tip of the bevelled sheath into the vessel;
 advancing the sheath to insert the entire bevelled portion of the sheath into the vessel; and
 rotating the leading edge of the bevelled tip of the sheath so that the leading edge of the sheath is at a substantially parallel relationship to the rear wall of the vessel.

23. The method according to claim 22 including the following step of removing the introducing catheter and guide wire from the vessel and leaving the sheath in place.

24. The method according to claim 22 wherein during the step of advancing the sheath to insert the entire bevelled portion of the sheath into the vessel, the sheath and the catheter are advanced as a unit.

25. The method according to claim 22 during the step of rotating the leading edge of the bevelled tip of the sheath, the sheath is rotated relative to the position of the catheter.

26. A method inserting a sheath with a bevelled distal end into a vessel comprising:
 puncturing the vessel with an instrument;
 dilating the puncture with a separate dilating catheter and;
 feeding a proximal cylindrical guide portion of the dilating catheter into the vessel through the puncture;
 introducing the bevelled end of the sheath into the vessel along said cylindrical guide by inserting the leading edge of the bevelled tip of the sheath in the undermost position relative to the puncture hole to engage the vessel at an acute angle between the guide element and the vessel wall; and
 inserting the entire bevelled portion of the sheath into the vessel.

* * * * *

EX PARTE REEXAMINATION CERTIFICATE (5860th)
United States Patent
Grayzel (10) Number: US 4,850,960 C1
(45) Certificate Issued: Aug. 21, 2007

(54) DIAGONALLY TAPERED, BEVELLED TIP INTRODUCING CATHETER AND SHEATH AND METHOD FOR INSERTION

(76) Inventor: Joseph Grayzel, 262 Fountain Rd., Englewood, NJ (US) 07631

Reexamination Request:
No. 90/006,446, Nov. 6, 2002

Reexamination Certificate for:
Patent No.: 4,850,960
Issued: Jul. 25, 1989
Appl. No.: 07/071,040
Filed: Jul. 8, 1987

(51) Int. Cl.
- A61M 31/00 (2006.01)
- A61M 5/178 (2006.01)
- A61M 25/00 (2006.01)
- A61M 5/32 (2006.01)

(52) U.S. Cl. .............. 604/510; 604/158; 604/528; 604/194

(58) Field of Classification Search .............. 604/510, 604/158, 528, 194
See application file for complete search history.

(56) References Cited

U.S. PATENT DOCUMENTS

| | | |
|---|---|---|
| 2,024,982 A | 12/1935 | Scott |
| 2,269,963 A | 1/1942 | Wappler |
| 2,512,569 A | 6/1950 | Saffir |
| 2,702,037 A | 2/1955 | Walter |
| 2,828,744 A | 4/1958 | Hirsch et al. |
| 2,842,133 A | 7/1958 | Uhma |
| 2,847,995 A | 8/1958 | Adams |
| 3,071,135 A * | 1/1963 | Baldwin et al. .......... 604/274 |
| 3,094,122 A | 6/1963 | Gauthier et al. |
| 3,185,151 A | 5/1965 | Czorny |
| 3,204,634 A | 9/1965 | Koehn |
| 3,313,299 A | 4/1967 | Spademan |
| 3,358,684 A | 12/1967 | Marshall |
| 3,478,435 A | 11/1969 | Cook |
| 3,536,073 A | 10/1970 | Farb |

(Continued)

FOREIGN PATENT DOCUMENTS

| | | |
|---|---|---|
| EP | 0 244 818 A2 | 11/1987 |
| JP | 59-227432 | 5/1986 |
| JP | 61-105744 | 5/1986 |

OTHER PUBLICATIONS

Tadavarthy, S. Murthy et al., "Kimray–Greenfield Vena Cava Filter: Percutaneous Introduction", RADIOLOGY, vol. 151, No. 2, 525–6.*

Gray's anatomy 1918, FIG. 577—The venæ cavæ and azygos veins, with their tributaries.*

Dotter, Charles T., et al., "The 'Nonsurgical' Treatment of Iliofemoral Arterosclerotic Obstruction", Radiology 86:871–875. May, 1966.

(Continued)

*Primary Examiner*—Beverly M. Flanagan (57) ABSTRACT

The present invention provides an improved introduction-dilating catheter which may also be applied to facilitate insertion of catheters of all types and functional purposes. The catheter has a tapered portion which is, in turn, connected to a bevelled tip portion to facilitate insertion of the catheter into a pre-existing puncture aperture. The bevelled tip portion is finished to remove any points capable of puncturing or any edges capable of injuring the tissues by the application of only a small force. Indicia means are provided to enable the practioner using the introduction-dilation catheter to determine the orientation of the tip of the catheter so that the leading point of the bevelled tip will initiate engagement with the vascular puncture cut and enter the vessel in the acute angle formed between the guide wire and the vessel wall. Additionally, after entry of the entire tip, the indicia means allow the introducing catheter to be reoriented so as to keep the bevel parallel to the wall of a vessel.

U.S. PATENT DOCUMENTS

| | | | |
|---|---|---|---|
| 3,538,918 A | 10/1970 | Englesher et al. | |
| 3,550,591 A | 12/1970 | MacGregor | |
| 3,570,485 A | 3/1971 | Reilly | |
| 3,584,624 A | 6/1971 | de Ciutiis | |
| 3,598,118 A | 8/1971 | Warren | |
| 3,605,750 A | 9/1971 | Sheridan et al. | |
| 3,631,990 A | 1/1972 | Redmer | |
| 3,633,579 A | 1/1972 | Alley | |
| 3,656,486 A | 4/1972 | Robertson | |
| 3,662,457 A | 5/1972 | Gores | |
| 3,662,754 A | 5/1972 | Halloran | |
| 3,675,639 A | 7/1972 | Cimber | |
| 3,682,166 A | 8/1972 | Jacobs | |
| 3,693,624 A | 9/1972 | Shiley et al. | |
| 3,703,174 A | 11/1972 | Smith | |
| 3,804,097 A | 4/1974 | Rudie | |
| 3,807,097 A | 4/1974 | Rudie | |
| 3,867,937 A | 2/1975 | Schwartz | |
| 3,877,429 A | 4/1975 | Rasumoff | |
| 3,882,863 A | 5/1975 | Samoff et al. | |
| 3,887,429 A | 6/1975 | Schmid et al. | |
| 3,903,885 A | 9/1975 | Fuchs | |
| 3,937,220 A | 2/1976 | Coyne | |
| 3,941,119 A | 3/1976 | Corrales | |
| 3,955,558 A | 5/1976 | Fuisz | |
| 3,965,901 A | 6/1976 | Penny et al. | |
| 3,993,079 A | 11/1976 | De Gatztanondo | |
| 3,995,628 A | 12/1976 | Gula et al. | |
| 4,020,837 A | 5/1977 | Larson | |
| 4,068,659 A | 1/1978 | Moorehead | |
| 4,068,660 A | 1/1978 | Beck | |
| 4,069,814 A | 1/1978 | Clemens | |
| 4,072,146 A | 2/1978 | Howes | |
| 4,096,860 A | 6/1978 | McLaughlin | |
| 4,098,275 A | 7/1978 | Consalvo | |
| 4,134,402 A | 1/1979 | Mahurkar | |
| 4,135,622 A | 1/1979 | Glick | |
| 4,166,469 A | 9/1979 | Littleford | |
| 4,180,068 A | 12/1979 | Jacobsen et al. | |
| 4,193,400 A | 3/1980 | Loveless et al. | |
| 4,195,624 A | 4/1980 | Douglas | |
| 4,205,675 A | 6/1980 | Vaillancourt | |
| 4,217,895 A | 8/1980 | Sagae et al. | |
| 4,239,042 A | 12/1980 | Asai | |
| 4,243,050 A | 1/1981 | Littleford | |
| 4,246,897 A | 1/1981 | Muto | |
| 4,274,408 A | 6/1981 | Nimrod | |
| 4,279,252 A | 7/1981 | Martin | |
| 4,299,217 A | 11/1981 | Sagae et al. | |
| 4,306,563 A | 12/1981 | Iwatschenko | |
| 4,314,555 A | 2/1982 | Sagae | |
| 4,323,072 A | 4/1982 | Rosenbluth et al. | |
| 4,327,709 A | 5/1982 | Hanson et al. | |
| 4,327,722 A * | 5/1982 | Groshong et al. | 604/510 |
| 4,345,606 A | 8/1982 | Littleford | |
| 4,362,156 A | 12/1982 | Feller, Jr. et al. | |
| 4,368,730 A | 1/1983 | Sharrock | |
| 4,381,008 A | 4/1983 | Thomas et al. | |
| 4,383,530 A | 5/1983 | Bruno | |
| 4,385,631 A | 5/1983 | Uthmann | |
| 4,403,617 A | 9/1983 | Tretinyak | |
| 4,444,185 A | 4/1984 | Shugar | |
| 4,445,893 A | 5/1984 | Bodicky | |
| 4,451,252 A | 5/1984 | Martin | |
| 4,468,224 A | 8/1984 | Enzmann et al. | |
| 4,473,067 A | 9/1984 | Schiff | |
| RE31,855 E | 3/1985 | Osborne | |
| 4,525,157 A | 6/1985 | Vaillancourt | |
| 4,529,399 A | 7/1985 | Groshong et al. | |
| 4,555,243 A | 11/1985 | Markham | |
| 4,565,545 A | 1/1986 | Suzuki | |
| 4,567,882 A | 2/1986 | Heller | |
| 4,568,329 A | 2/1986 | Mahurkar | |
| 4,576,142 A | 3/1986 | Schiff | |
| 4,581,025 A | 4/1986 | Timmermans | |
| 4,582,067 A | 4/1986 | Silverstein et al. | |
| 4,588,398 A | 5/1986 | Daugherty et al. | |
| 4,609,370 A | 9/1986 | Morrison | |
| 4,612,939 A | 9/1986 | Robertson | |
| 4,617,019 A | 10/1986 | Fecht et al. | |
| 4,622,968 A | 11/1986 | Persson | |
| 4,623,327 A | 11/1986 | Mahurkar | |
| 4,629,450 A | 12/1986 | Suzuki et al. | |
| 4,631,059 A | 12/1986 | Wolvek et al. | |
| 4,634,432 A | 1/1987 | Kocak | |
| 4,645,491 A | 2/1987 | Evans | |
| 4,650,472 A | 3/1987 | Bates | |
| 4,662,870 A | 5/1987 | Augustine et al. | |
| 4,684,369 A | 8/1987 | Wildemeersch | |
| 4,710,171 A | 12/1987 | Rosenberg | |
| 4,716,901 A | 1/1988 | Jackson et al. | |
| 4,721,506 A | 1/1988 | Teves | |
| 4,744,364 A | 5/1988 | Kensey | |
| 4,759,746 A | 7/1988 | Straus | |
| 4,760,847 A | 8/1988 | Vaillancourt | |
| 4,772,264 A | 9/1988 | Cragg | |
| 4,772,266 A | 9/1988 | Groshong | |
| 4,772,268 A | 9/1988 | Bates | |
| 4,774,949 A | 10/1988 | Fogarty | |
| 4,775,367 A | 10/1988 | Schmidt | |
| 4,790,817 A | 12/1988 | Luther | |
| 4,809,713 A | 3/1989 | Grayzel | |
| 4,838,879 A | 6/1989 | Tanabe et al. | |
| 4,842,589 A | 6/1989 | Fecht et al. | |
| 4,846,799 A | 7/1989 | Tanaka et al. | |
| 4,874,375 A | 10/1989 | Ellison | |
| 4,878,495 A | 11/1989 | Grayzel | |
| 4,882,777 A | 11/1989 | Narula | |
| 4,921,479 A | 5/1990 | Grayzel | |

OTHER PUBLICATIONS

Dotter, Charles T., et al., "Transluminal Angioplasty", motion picture, (video) University of Oregon Medical School, Protland, Oregon, 1969.

Hettler, M., "Angiographische Probleme und Moglichkeiten" *Fortschritte Auf Dem Gebiete Der Rontgenstrahlen Und Der Nuklearmedizin Diagnostik, Physik, Biologie, Therapie,* 1960, pp. 198–206, vol. 92, Stuttgart, Germany. (Advances in the Fields of Radiology and Nuclear Medicine Diagnostics, Physics, Biology, Therapy, 1960 vol. 92 with 848 illustrations, Georg Thieme Publishing—Stutgart).

Baud, F. et al., "Mise en Place Per–Operatoire d'un Catheter de Prise de Pression de l'Oreillette Gauche" *La Presse Medicale,* Dec. 10, 1983, pp. 2881–2882, vol. 45, No. 12, Paris, France. (The Medical Press, Biomedical Library, Feb. 6, 1984, vol. 45, Dec. 10, 1983).

Tilkian, A., et al., *Cardiovascular Procedures, Diagnostic Techniques and Therapeutic Procedures,* 1986, pp. 131–46, C.V. Mosby Co. St. Louis, Missouri, USA.

*Cardiac Catherization, Angiography, and Intervention,* pp. 185–197, Editors: Grossman et al., Lea & Febiger, Philadelphia, Pennsylvania, USA (edition and date unknown; best available copy).

Heading *General Cardiac Catheterization,* Chapter: Catheters, Sheaths, Guidewires, Needles, and Related Equipment, miscellaneous pages (source and data unknown).

Heading: *Diagnostic Cardiac Catheterization*, Chapter: Coronary Angiography, pp. 278–287 (source and date unknown).

Heading: *Part XXI Diagnostic Techniques of Cardiac Catheterization and Vascular Angiography*, Chapter 138: Techniques of Cardiac Catheterization Including Coronary Angiography. pp. 2403–2408 (source and date unknown).

Swan, H. et al., "Catheterization of the Heart in Man with Use of a Flow–Directed Balloon–Tipped Catheter", *The New England Journal of Medicine*, Aug. 27, 1970, pp. 447–451, vol. 283, No. 9, The Massachusetts Medical Society, Boston, Massachusetts, USA.

Rizk, G, et al., "The Percutaneous Method of Introducing the Caval Umbrella", *The American Journal of Roentgenology, Radium Therapy and Nuclear Medicine*, Apr. 1973, pp. 903–909, vol. 117, No. 4, Charles C Thomas, Springfield, Illinois, USA.

Knight, L., et al, "Alternate Method for Introduction of the Inferior Vena Cava Filter", *Surgery Gynecology & Obstetrics*, 1974, pp. 763–764, vol. 138, The Franklin H. Martin Memorial Foundation, Chicago, Illinois, USA.

Foote, G., et al., "Pulmonary Complications of the Flow–Directed Balloon–Tipped Catheter", *The New England Journal of Medicine*, Apr. 25, 1974, pp. 927–931, vol. 290, No. 17, The Massachusetts Medical Society, Boston, Massachusetts, USA.

Bean, W., et al., "T–Tube Tract Dilation for Removal of Large Billiary Stones", *Radiology*, May 1975, pp. 485–488, vol. 115, Chicago, Illinois, USA, figures too dark.

Swan, H., et al, "Use of Balloon Floatation Catheters in Critically Ill Patients", *The Surgical Clinics of North America*, Jun. 1975, pp. 501–520, vol. 55, No. 3, W.B. Saunders Company, Philadelphia, Pennsylvania, USA.

Rösch, W., et al, "A New Catheter for Endoscopic Manometry of Oddl's Sphincter", *Endoscopy*, 1977, pp. 31–33, vol. 9, Georg Thieme Publishers, Stuttgart, Germany.

Gutschik, E, et al., "Experimental Endocarditis in Rabbits", *Acta Pathologica Eet Microbologica Scandinavica: Section B*, 1978, pp. 215–221, vol. 86, Copenhagen, Denmark.

Neumann, H., et al, "New Markings of Central Venous Catheters, an Improvement for Localisation on X–Ray Pictures", *Radiologie*, Oct. 1981, pp. 493–495, vol. 21, No. 10, Springer–Verlag, Berlin, Germany.

Bennett, E, et al., "Comparison of Flow Differences among Venous Cannulas", *The Annals of Thoracic Surgery*, Jul. 1983, pp. 59–65, vol. 36, No. 1, Little Brown and Co., Boston, Massachusetts, USA.

Horstt, M., et al., "The Risks of Pulmonary Arterial Catheterization", *Surgery: Gynecology & Obstetrics*, Sep. 1984, pp. 229–232, vol. 159, No. 3, The Franklin H. Martin Memorial Foundation, Chicago, Illinois, USA.

Beutel, E. et al., "A Useful Technique for Computerized Tomography Directed Needle Biopsy", *Surgery Gynecology and Obstetrics*, May 1986, pp. 491–492, vol. 162, No. 5, The Franklin H. Martin Memorial Foundation, Chicago, Illinois, USA.

Capri Sun advertisements, *Woman's Day*, Sep. 9, 1986, Hachette Magazines, Inc., Boulder, Colorado, USA.

Frei, E., et al., "The POD and its Applications", *Medical Research Engineering*, 1966, pp. 11–18, 4th Quarter, Little Falls, NJ, USA.

Seldinger, S., "Catheter Replacement of the Needle in Percutaneous Arteriography", *Acta Radiologica*, May 1953, pp. 368–376, vol. 39, Stockholm, Sweden.

Desilets, D. et al., "A New Method of Percutaneous Catheterization" *Radiology*, Jul. 1965, pp. 147–148, vol. 85, No. 1, The Radiological Society of North America, Inc., Easton, Pennsylvania, USA.

Desilets, D. et al., "A New Method of Percutaneous Catheterization" *The American Journal of Roentgenology Radium Therapy and Nuclear Medicine*, Jun. 1966, pp. 519–522, vol. 97, Charles C. Thomas, Springfield, Illinois, USA.

Vellani et al., "Endocardial Pacing: A Percutaneous Method Using the Subclavian Vein" *British Heart Journal*, 1969, pp. 106–111, vol. 31, London, England.

Howard–Jones N., "The Origins of Hypodermic Medication" *Scientific American*, Jan. 1971, pp. 96–102, USA.

Jachuck et al., "Permanent Cardiac Pacing Through the Subclavian Vein" *The British Journal of Surgery*, Dec. 1974, pp. 373–376, vol. 61, The Williams & Wilkins Co., Baltimore, Maryland, USA.

Knight, L. et al., "Percutaneous Introduction of Inferior Vena Cava Filter: Human Experience" *Radiology*, Apr. 1974, pp. 61–63, vol. 111, No. 1, Chicago, Illinois, USA.

Friesen, A. et al., "Percutaneous Insertion of a Permanent Transvenous Pacemaker Electrode Through the Subclavian Vein" *The Canadian Journal of Surgery*, Mar. 1977, pp. 131–135, vol. 20, No. 2, The Canadian Medical Association, Canada.

Barry, W., "Left Heart Catheterization and Angiography Via the Percutaneous Femoral Approach Using an Arterial Sheath" *Catheterization and Cardiovascular Diagnosis*, 1979, pp. 401–409, vol. 5, No. 4.

Hillis, D., "Percutaneous Left Heart Catheterization and Coronary Arteriography Using a Femoral Artery Sheath" *Catheterization and Cardiovascular Diagnosis*, 1979, pp. 393–399, vol. 5, No. 4, USA.

Boskovski, N. et al., *Anaesthesia Journal of the Association of Great Britain & Ireland*, Feb. 1982, pp. 216–217, vol. 37, No. 2, London, England.

Coles, J. et al., "Cardioplegia for Severe Coronary Artery Disease: An Improved Technique Using Direct Coronary Artery Infusion" *The Annals of Thoracic Surgery*, Mar. 1982, pp. 234–247, vol. 33, No. 3, USA.

Rusnak, B. et al., "An Improved Dilator System for Percutaneous Nephrostomies" *Radiology*, Jul. 1982, p. 174, vol. 144, No. 1, Chicago, Illinois, USA.

Sheep, R. et al., "Fatal Cardiac Tamponade Occurrence With Other Complications After Left Internal Jugular Vein Catheterization" *The Journal of the American Medical Association*, Oct. 1, 1982, pp. 1632–1635, vol. 248, No. 13, USA.

Choy, D. et al., "Transluminal Laser Catheter Angioplasty" *The American Journal of Cardiology*, Dec. 1982, pp. 1206–1208, vol. 50, No. 6, USA.

Cragg, A. et al., "Nonsurgical Placement of Arterial Endoprostheses: A New Technique Using Nitinol Wire" *Radiology*, Apr. 1983, pp. 261–263, vol. 147, No. 1, Chicago, Illinois, USA.

Andriole, J. et al., "Biopsy Needle Characteristics Assessed in the Laboratory", *Radiology*, Sep. 1983, pp. 659–662, vol. 148, No. 3, Chicago, Illinois, USA.

Jackson, D. et al., "American National Standard for Medical Material—Luer Taper Fittings—Performance" *American National Standard*, 1984, pp. 7–15, American National Standards Institute, Inc., New York, New York, USA.

Tadavarthy, M. et al., "Kimray–Greenfield Vena Cava Filter: Percutaneous Introduction" *Radiology,* May 1984, pp. 525–526, vol. 151, No. 2, USA.

Ilia, R. et al., "Percutaneous Left Heart Catheterization and Coronary Arteriography With and Without an Arterial Sheath in Patients Without Peripheral Vascular Disease" *Catheterization and Cardiovascular Diagnosis,* 1985, pp. 463–466, vol. 11, No. 5, USA.

Canaud, B. et al., "Internal Jugular Vein Cannulation Using 2 Silastic Catheters A New, Simple and Safe Long–Term Vascular Access for Extracorporeal Treatment" *Nephron,* Jun. 1986, pp. 133–138, vol. 43.

Mohr, L. et al., "Catheterization of Synthetic Vascular Grafts" *Journal of Vascular Surgery,* Jun. 1986, pp. 854–856, vol. 3, No. 6, USA.

"Diagnostic and Interventional Products", Cook Incorporated, pp. 17–19, 1986.

Grollier, G. et al., "Anterograde Percutaneous Transseptal Valvuloplasty in a Case of Severe Calcific Aortic Stenosis" *European Heart Journal,* Feb. 1987, pp. 190–193, vol. 8, No. 2.

* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1, 3–12, 15 and 17–26 is confirmed.

Claims 2, 13, 14 and 16 are cancelled.

\* \* \* \* \*